US00PP18981P2

(12) United States Plant Patent

Kawashima et al.

(10) Patent No.: US PP18,981 P2

(45) Date of Patent: Jun. 24, 2008

(54) *OSTEOSPERMUM* PLANT NAMED 'KAKEGAWA AU19'

(50) Latin Name: *Osteospermum hybrida*
Varietal Denomination: Kakegawa AU19

(75) Inventors: Moriya Kawashima, Matsumoto (JP); Akinobu Ui, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/703,587

(22) Filed: Feb. 7, 2007

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
(74) *Attorney, Agent, or Firm*—Jondle & Associates, P.C.

(57) ABSTRACT

An *Osteospermum* cultivar particularly distinguished by its deep purple flower color, resistance to fading, basal branching and compact habit, and ability to flower in hot temperatures is disclosed.

1 Drawing Sheet

Genus and species: *Osteospermum hybrida.*
Variety denomination: 'Kakegawa AU19'.

BACKGROUND OF THE NEW PLANT

'Kakegawa AU19' originated from a hybridization of proprietary hybrid *Osteospermum* breeding line '2K-MY-6' (unpatented) and proprietary hybrid *Osteospermum* line '9PR-2' (unpatented) in Kakegawa, Japan. The male parent, '9PR-2', has a deep purple flower color and a plant growth habit with less branching. The female parent, '2K-MY-6', has a purple flower color and strong blooming ability.

In 2001, the two *Osteospermum* lines were crossed and 18 seeds were obtained. The seeds were sown and out of the 18 seeds, 13 plants were grown in pots for evaluation. Out of 13 $F_1$ lines, line 'K3-8' was selected which has a deep purple flower color with resistance to fading and a basal branching and compact plant growth habit.

In fall 2002, line 'K3-8' was vegetatively propagated with cuttings and re-evaluated in an open filed and a greenhouse. It was discovered that the plant line maintained its blooming power under high temperature conditions making it a heat tolerant plant variety. In spring 2004, plants were evaluated again in pots and in an open field. The selection subsequently was named 'Kakegawa AU19' and found to retain its distinctive characteristics through successive asexual propagations in Kakegawa, Japan and Salinas, Calif.

Plant Breeder's Rights for this cultivar were applied for in Canada on Mar. 31, 2006.

SUMMARY OF THE INVENTION

The following are the most outstanding and distinguishing characteristics of this new cultivar when grown under normal horticultural practices in Kakegawa, Japan.

1. Deep purple flower color;
2. Resistance to fading;
3. Basal branching and compact growth habit; and
4. Ability to flower in hot temperatures.

DESCRIPTION OF PHOTOGRAPHS

This new *Osteospermum* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
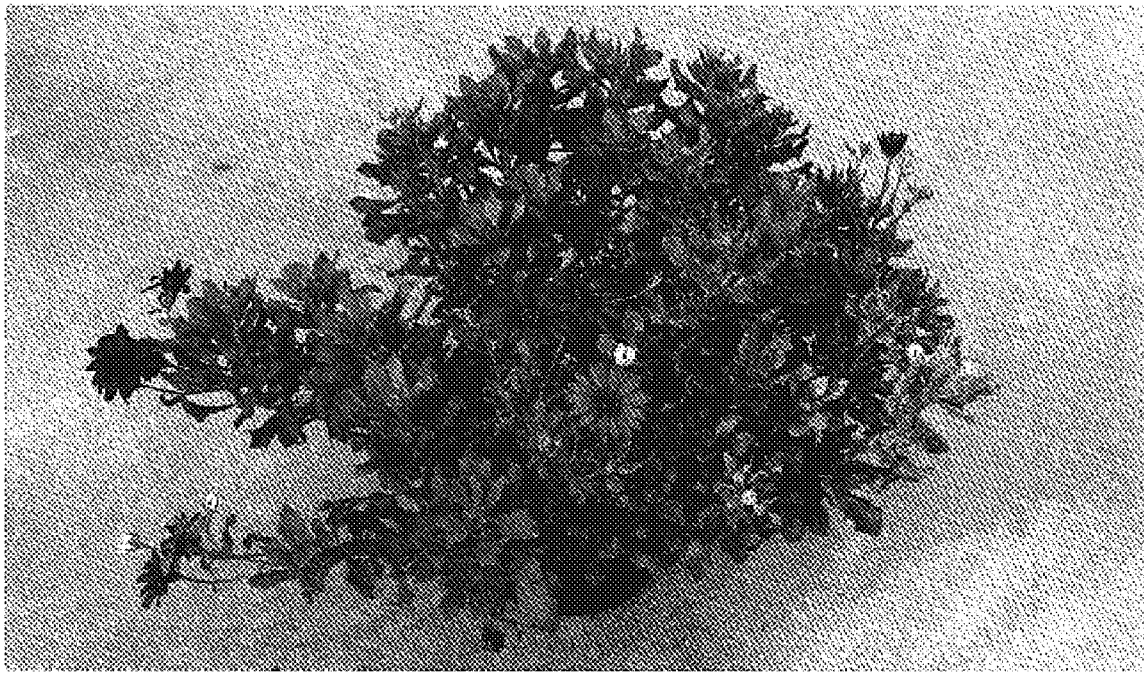
FIG. 1 shows overall plant habit.
Figure 2:
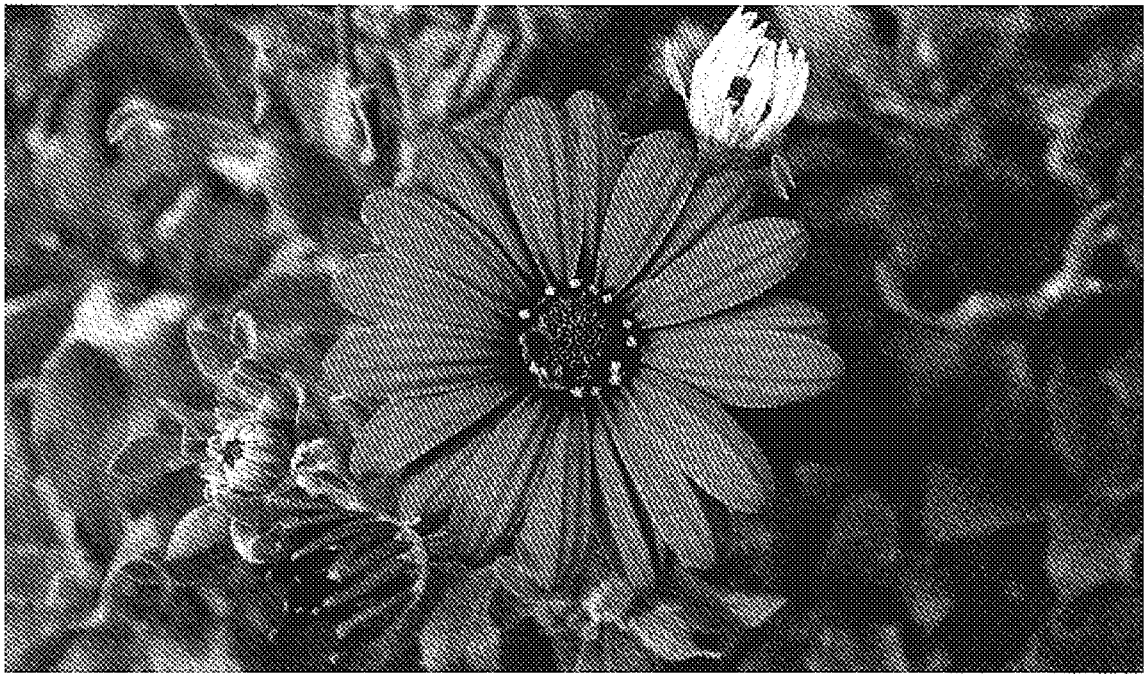
FIG. 2 shows the mature inflorescence.

The following detailed descriptions set forth the distinctive characteristics of 'Kakegawa AU19'. The data which define these characteristics were collected from asexual reproductions carried out in Salinas, Calif. Data was collected on plants grown approximately five months from transplanting rooted cuttings into 6-inch pots under greenhouse conditions in Salinas, Calif. Color references are to the R.H.S. Colour Chart of The Royal Horticultural Society of London (R.H.S.).

DESCRIPTION OF THE NEW PLANT

Classification:

*Family.*—Compositae.

*Botanical.*—*Osteospermum hybrida.*

Parentage:

*Female parent.*—Hybrid proprietary *Osteospermum* line '2K-MY-06' (unpatented).

*Male parent.*—Hybrid proprietary *Osteospermum* line '9PR-2' (unpatented).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) on DIP 'N GROW root-inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150–200 ppm fertilizer solution containing 18% nitrogen, 8% phosphorus and 18% potassium. The soil is allowed to dry between waterings. During the first few weeks after transplanting, the plants should have evening temperatures around 15–18° C. for good root growth. When plants reach 7.5–10 cm in height they are pinched back to 5–6 leaves to promote branching. Spring and summer daytime high temperatures in Salinas, Calif., where the data was collected, range from 16–25° C.

*Time to bloom from propagation.*—Approximately four weeks when rooted vegetative cuttings are transferred to a 16 cm. diameter pot. Flowering season is all year in the United States. Vernalization is not required to induce flowering.

Plant description:

*Habit.*—Upright and branching.
*Life cycle.*—Perennial.
*Form.*—Branching, dense.
*Height.*—30 cm to 40 cm.
*Width.*—50 cm to 60 cm.

Stems:

*Internode length.*—1.5 cm to 2.0 cm.
*Stem description.*—Strong, erect.
*Stem diameter.*—0.3 to 0.4 cm.
*Stem color.*—RHS 145B (Yellow-green).
*Pubescence.*—Sparse.
*Pubescence shape.*—Linear.
*Pubescence color.*—RHS N155A (White).

Leaves:

*Arrangement.*—Alternate.
*Shape.*—Oblanceolate.
*Apex.*—Acute.
*Base.*—Decurrent.
*Margin.*—Serrate.
*Venation.*—Pinnate.
*Surface.*—Dull, smooth.
*Surface pubescence.*—Present.
*Length.*—5.5 cm to 7.5 cm.
*Width.*—2.5 cm to 3.7 cm.
*Thickness.*—0.1 cm.
*Color.*—Upper surface: RHS 139A (Green). Lower surface: RHS 137B (Green).
*Venation color.*—Upper surface: RHS 138B (Green). Lower surface: RHS 138B (Green).

Inflorescence:

*Type.*—Capitulum (head); Disc florets are perfect and ray florets are carpellate.
*Flowering habit.*—Determinate.
*Lastingness of flowers.*—3 to 4 days.
*Fragrance.*—None.
*Seed production.*—None observed.
*Diameter.*—6.0 cm to 6.5 cm.
*Depth.*—1.5 cm to 2.0 cm.
*Petal number.*—16 to 19 per inflorescence.
*Disc diameter.*—1.0 cm to 1.2 cm.
*Disc floret number.*—65 to 75 per head.
*Peduncle length.*—9.0 cm to 12.5 cm.
*Peduncle diameter.*—0.2 cm.
*Peduncle color.*—RHS 138B (Green).
*Peduncle texture.*—Dull, slight pubescence.
*Phyllaries.*—Arrangement: 14 per inflorescence, free, arranged symmetrically. Length: 0.9 cm to 1.0 cm. Width: 0.1 cm to 0.15 cm. Apex: Acute. Margin: Entire. Shape: Linear, acute. Color: Upper surface: RHS 138A (Green). Lower surface: RHS 138B (Green).

Ray florets (Ligules):

*Corolla.*—One petal per ray floret; only the outer row of florets are the ray florets.
*Number of ray florets per inflorescence.*—19.
*Petal length.*—3.0 cm to 3.4 cm.
*Petal width.*—0.3 cm to 0.45 cm.
*Petal shape.*—Spatulate.
*Petal apex.*—Obtuse with a notched tip.
*Petal margin.*—Entire.
*Petal color.*—Upper surface: RHS 61C (Red-purple) with RHS N79B (Purple) streaks. Lower surface: RHS 84B (Violet) with RHS 79A (Purple) streaks.
*Petal pubescence.*—Glabrous.
*Ovary.*—Superior.
*Pistil form.*—One style with two stigma branches.
*Pistil length.*—0.3 cm.
*Stigma color.*—RHS N92A (Violet-purple to almost black).
*Style color.*—RHS N92A (Violet-purple to almost black).

Disc florets:

*Color.*—RHS N89A (Violet-blue).
*Shape.*—Tubular.
*Apex.*—Tubular.
*Surface.*—Smooth, shiny.
*Size.*—Length: 0.4 cm. Width: 0.1 cm.
*Pistil form.*—One style with two stigma branches.
*Ovary.*—Superior.
*Style color.*—RHS 82A (Purple-violet).
*Stigma color.*—RHS N92A (Violet-purple to almost black).
*Stamens.*—5, fused into a single tube.
*Anther color.*—RHS N92A (Violet-purple to almost black).
*Pollen color.*—RHS 23A (Yellow-orange).

Disease and insect resistance: Very disease resistant, however, plants are susceptible to aphids, thrips, whiteflies and worms.

COMPARISON WITH PARENTAL LINES AND KNOWN CULTIVARS

'Kakegawa AU19' is a distinct variety of *Osteospermum* owing to its deep purple flower color, resistance to fading, basal branching and compact growth habit and its ability to flower in hot temperatures. 'Kakegawa AU19' is distinguished from its parents primarily by ray floret color and plant growth habit as described in Table 1 below (color references are to The Royal Horticultural Society Colour Chart, 4$^{th}$ edition):

| Characteristic | 'Kakegawa AU19' | Male Parent '9PR-2' | Female Parent '2K-MY-6' |
|---|---|---|---|
| Ray floret (ligule) color, upper surface: | Deep Purple | Purple | Deep purple |
| Habit | Compact, basal branching | Compact | Less branching |

'Kakegawa AU19' is most similar to the *Osteospermum* plant named 'Kakegawa AU3' (U.S. Plant Pat. No. 12,778); however, there are differences as described in Table 2 below (color references are to The Royal Horticultural Society Colour Chart, 4$^{th}$ edition):

TABLE 2

| Characteristic | 'Kakegawa AU19' | 'Kakegawa AU3' |
|---|---|---|
| Ray floret (ligule) color, upper surface: | RHS 61C (Red-purple) with RHS N79B (Purple) streaks | RHS 71A (Red-purple) |
| Habit | Compact | Vigorous, well branched |

I claim:

1. A new and distinct cultivar of *Osteospermum* plant as shown and described herein.

* * * * *